US00PP22556P2

(12) United States Plant Patent
Heffron et al.

(10) Patent No.: US PP22,556 P2
(45) Date of Patent: Mar. 6, 2012

(54) ***VERBENA* PLANT NAMED 'BALAZVELU'**

(50) Latin Name: *Verbena×hybrida*
Varietal Denomination: Balazvelu

(75) Inventors: Leslie Heffron, Granite Falls, NC (US); Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/924,308

(22) Filed: Sep. 24, 2010

(51) Int. Cl.
*A01H 5/00* (2006.01)

(52) U.S. Cl. ..... Plt./308

(58) Field of Classification Search ..... Plt./308
See application file for complete search history.

*Primary Examiner* — Susan McCormick Ewoldt

(74) *Attorney, Agent, or Firm* — Audrey Charles

(57) ABSTRACT

A new and distinct cultivar of *Verbena* plant named 'Balazvelu', characterized by its dark violet-blue colored flowers, dark green-colored foliage, and moderately vigorous, trailing, spreading growth habit, is disclosed.

1 Drawing Sheet

Latin name of genus and species of plant claimed: *Verbena×hybrida.*

Variety denomination: 'Balazvelu'.

BACKGROUND OF THE INVENTION

The present invention relates to a new and distinct cultivar of *Verbena* plant botanically known as *Verbena×hybrida* and hereinafter referred to by the cultivar name 'Balazvelu'.

The new cultivar originated in a controlled breeding program in Arroyo Grande, Calif. during March 2006. The objective of the breeding program was the development of *Verbena* cultivars with unique flower coloration and a vigorous trailing, spreading growth habit.

The new *Verbena* cultivar was the result of a self-pollination of the proprietary *Verbena×hybrida* breeding selection designated 2886-2, not patented, characterized by its dark purple-colored flowers with no eye, dark green-colored foliage, and moderately vigorous, trailing growth habit. The new cultivar was discovered and selected as a single flowering plant within the progeny of the above stated self-pollination during November 2006 in a controlled environment at Arroyo Grande, Calif.

Asexual reproduction of the new cultivar by terminal stem cuttings since November 2006 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balazvelu' as a new and distinct cultivar of *Verbena* plant:

1. Dark violet-blue colored flowers;
2. Dark green-colored foliage; and
3. Moderately vigorous, trailing, spreading growth habit.

Plants of the new cultivar differ from plants of the parent primarily in the flower color and leaf size. Plants of the new cultivar have deeper violet-blue colored flowers and have smaller leaves.

Of the many commercially available Verbena cultivars, the most similar in comparison to the new cultivar is LANAI Deep Purple 'Lan Depur', U.S. Plant Pat. No. 15,606. However, in side by side comparisons, plants of the new cultivar differ from plants of 'Lan Depur' in at least the following characteristics:

1. Plants of the new cultivar have a flower color that is darker than plants of 'Lan Depur'; and
2. Plants of the new cultivar have fewer main branches than plants of 'Lan Depur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balazvelu'. The plants were grown in 4-inch pots for 7 weeks in a greenhouse at West Chicago, Ill. Plants were given one pinch at transplant.

DETAILED BOTANICAL DESCRIPTION

Figure 1:
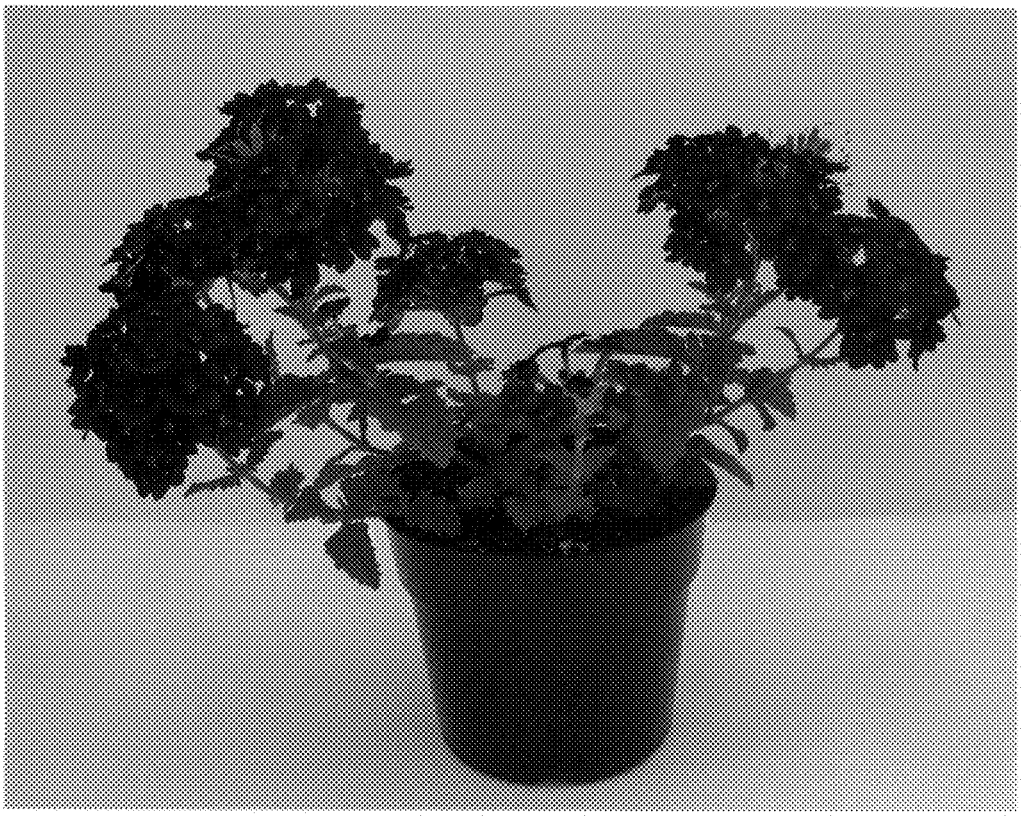
FIG. 1 illustrates a side view of the overall growth and flowering habit of 'Balazvelu'.
Figure 2:
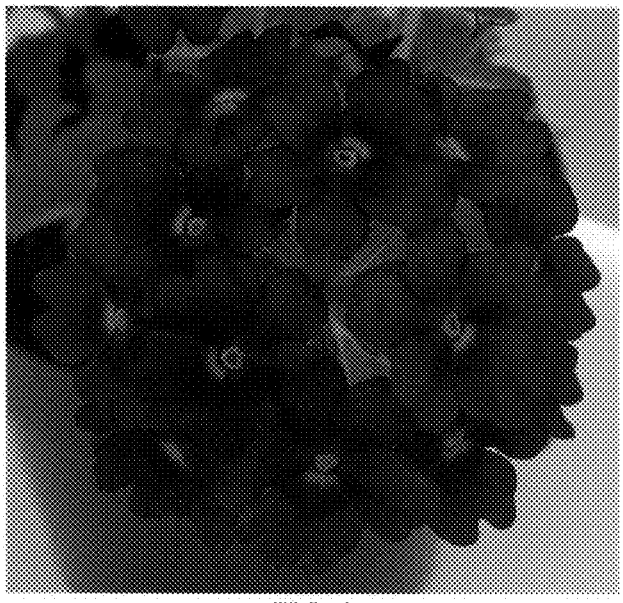
FIG. 2 illustrates a close-up view of an individual inflorescence of 'Balazvelu'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in June 2010 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 7 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Verbena×hybrida* cultivar Balazvelu.

Parentage:

*Female and male parent.*—Proprietary *Verbena×hybrida* breeding selection designated 2886-2, not patented.

Propagation:

*Type cutting.*—Terminal stem.

*Time to initiate roots.*—Approximately 6 to 9 days.

*Time to produce a rooted cutting.*—Approximately 24 to 28 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, and trailing, spreading.

*Size.*—Height from soil level to top of plant plane: Approximately 12.6 cm. Width: Approximately 30.7 cm.

*Branching habit.*—Freely branching, pinching enhances basal branching. Quantity of main branches per plant: Approximately 4.

*Branch.*—Shape: Square in cross section. Strength: Strong. Length: Approximately 17.2 cm. Diameter: Approximately 4.0 mm. Length of central internode: Approximately 1.7 cm. Texture: Densely pubescent with a mixture of glandular and nonglandular hairs. Gland color: Colorless, transparent. Color of young and mature stems: 144A with an overlay of 187A.

Foliage description:

*General description.*—Quantity of leaves per main branch: Approximately 10. Fragrance: None. Form: Simple. Arrangement: Opposite.

*Leaves.*—Aspect: Perpendicular to stem. Shape: Ovate. Margin: Serrate. Apex: Acute. Base: Truncate. Venation pattern: Pinnate. Length of mature leaf: Approximately 4.2 cm. Width of mature leaf: Approximately 2.9 cm. Texture of upper surface: Sparsely pubescent. Texture of lower surface: Densely pubescent on venation with a mixture of glandular and nonglandular hairs. Gland color: Colorless, transparent. Color of upper surface of young and mature foliage: Darker than 137A with venation of 144D. Color of lower surface of young and mature foliage: 138B with venation of 145C.

*Petiole.*—Length: Approximately 6.0 mm. Diameter: Approximately 2.0 mm. Texture: Densely pubescent. Color: 144D.

Flowering description:

*Flowering habit.*—'Balazvelu' is freely flowering under outdoor growing conditions with substantially continuous blooming from spring through autumn and year-round in greenhouse environment.

*Lastingness of individual flower on the plant.*—Approximately 5 to 7 days.

Inflorescence description:

*General description.*—Type: Corymb. Shape: Hemispherical. Quantity per plant: Approximately 8. Fragrance: None. Length or height: Approximately 4.2 cm. Width: Approximately 6.2 cm. Quantity of fully open flowers per inflorescence: Approximately 23.

*Peduncle.*—Strength: Strong. Aspect: Erect. Length: Approximately 3.4 cm. Diameter: Approximately 2.0 mm. Texture: Densely pubescent on venation with a mixture of glandular and nonglandular hairs. Gland color: 86A, transparent. Color: 144A.

Flower description:

*General description.*—Type: Sessile, salverform.

*Bud.*—Rate of opening: Generally takes 2 to 3 days for bud to progress from first color to fully open flower. Quantity of unopened inflorescences per plant: Approximately 1.

*Bud just before opening.*—Shape: Elongated. globular at apex. Length: Approximately 1.3 cm. Diameter: Approximately 3.0 mm. Color: N92C.

*Corolla.*—Shape: Round. Diameter: Approximately 2.2 cm. Depth: Approximately 2.5 cm.

*Petals.*—Quantity: 5, fused at base forming a tube. Shape: Obovate. Appearance: Velvety. Margin: Entire. Apex: Emarginate. Length of upper petal from tube: Approximately 1.0 cm. Width of upper petal: Approximately 1.1 cm. Length of lateral petals from tube: Approximately 1.0 cm. Width of lateral petals: Approximately 9.0 mm. Length of lower petals from tube: Approximately 9.0 mm. Width of lower petals: Approximately 8.0 mm. Texture of upper surface: Glabrous. Texture of lower surface: Sparsely pubescent with a mixture of glandular and nonglandular hairs. Gland color: Colorless, transparent. Color of upper surface when fully open: Darker than N92D; upper petal base of N87D. Color of lower surface when fully open: N87A. Whisker color surrounding the opening of the corolla tube: Mixture of pure white and N87D.

*Corolla tube.*—Length: Approximately 1.9 cm. Diameter at proximal end: Approximately 1.0 mm. Diameter at distal end: Approximately 2.0 mm. Texture of inner and outer surfaces: Densely pubescent. Color of inner surface: 145D at proximal end transitioning to 145B at distal end. Color of outer surface: 145D with a faint overlay of N87D at distal end.

*Calyx.*—Shape: Tubular with 5 acute tips. Length: Approximately 1.1 cm. Width: Approximately 2.0 mm.

*Sepals.*—Quantity per flower: 5, fused at base. Shape: Linear. Apex: Acute. Length: Approximately 1.1 cm. Width: Approximately 1.0 mm. Texture of inner surface: Densely pubescent. Texture of outer surface: Densely pubescent on venation with a mixture of glandular and nonglandular hairs. Gland color: Mixture of 86A and colorless, transparent. Color of upper and lower surfaces: 137A, transparent where margins fuse.

*Stipules.*—Shape: Lanceolate. Apex: Acute. Length: Approximately 4.0 mm. Width at base: Approximately 2.0 mm. Texture of inner surface: Glabrous. Texture of outer surface: Densely pubescent with a mixture of glandular and nonglandular hairs. Gland color: Colorless. Color of inner and outer surfaces: 144A at base transitioning to 137A at apex.

*Reproductive organs.*—Androecium: Stamen quantity: 4, didynamous. Stamen length of longer pair: Approximately 3.0 mm. Stamen length of shorter pair: Approximately 2.0 mm. Anther shape: Bilobed, ovoid. Anther length: Approximately 1.0 mm. Anther color: 154B. Pollen amount: Sparse. Pollen color: 154D. Gynoecium: Pistil quantity: 1 per flower. Pistil length: Approximately 1.7 cm. Stigma shape: Biparted. Stigma length: Less than 1 mm. Stigma color: 143A with an overlay of 187A. Style length: Approximately 1.6 cm. Style color: 144C transitioning to 144D at base. Ovary diameter: Approximately 1.0 mm. Ovary texture: Glabrous. Ovary color: N144C.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balazvelu', substantially as herein shown and described.

* * * * *